United States Patent
Barron et al.

(10) Patent No.: US 7,692,218 B2
(45) Date of Patent: Apr. 6, 2010

(54) METHOD FOR CREATING A FUNCTIONAL INTERFACE BETWEEN A NANOPARTICLE, NANOTUBE OR NANOWIRE, AND A BIOLOGICAL MOLECULE OR SYSTEM

(75) Inventors: Andrew R. Barron, Houston, TX (US); Dennis J. Flood, Oberlin, OH (US); Elizabeth A. Whitsitt, Houston, TX (US); Robin E. Anderson, Houston, TX (US); Graham B. I. Scott, Katy, TX (US)

(73) Assignees: William Marsh Rice University, Houston, TX (US); New Cyte, Inc., Sudbury, MA (US)

( * ) Notice: Subject to any disclaimer, the term of this patent is extended or adjusted under 35 U.S.C. 154(b) by 641 days.

(21) Appl. No.: 10/534,431

(22) PCT Filed: Nov. 19, 2003

(86) PCT No.: PCT/US03/37186

§ 371 (c)(1),
(2), (4) Date: Jan. 24, 2006

(87) PCT Pub. No.: WO2005/000735

PCT Pub. Date: Jan. 6, 2005

(65) Prior Publication Data

US 2006/0145194 A1    Jul. 6, 2006

Related U.S. Application Data

(60) Provisional application No. 60/427,616, filed on Nov. 19, 2002.

(51) Int. Cl.
*H01L 31/00* (2006.01)

(52) U.S. Cl. .................. 257/253; 257/414; 257/E51.04; 438/49; 977/936

(58) Field of Classification Search .................. 257/253
See application file for complete search history.

(56) References Cited

U.S. PATENT DOCUMENTS 5,162,279 A    11/1992    Miki (Continued)

FOREIGN PATENT DOCUMENTS

DE    10036897 C1    1/2002

(Continued)

OTHER PUBLICATIONS

PCT International Search Report Application No. PCT/US03/37186 dated Feb. 8, 2005 (2 p.).

(Continued)

*Primary Examiner*—Jerome Jackson, Jr.
(74) *Attorney, Agent, or Firm*—Conley Rose, P.C.; Rodney B. Carroll

(57) ABSTRACT

A field effect transistor and a method for making the same. In one embodiment, the field effect transistor comprises a source; a drain; a gate; at least one carbon nanotube on the gate; and a dielectric layer that coats the gate and a portion of the at least one carbon nanotube, wherein the at least one carbon nanotube has an exposed portion that is not coated with the dielectric layer, and wherein the exposed portion is functionalized with at least one indicator molecule. In other embodiments, the field effect transistor is a biochem-FET.

36 Claims, 1 Drawing Sheet

U.S. PATENT DOCUMENTS

| | | |
|---|---|---|
| 5,274,018 A | 12/1993 | Tanaka et al. |
| 5,308,661 A | 5/1994 | Feng et al. |
| 5,397,350 A | 3/1995 | Chow et al. |
| 5,416,188 A | 5/1995 | Chiang et al. |
| 5,420,081 A | 5/1995 | Mattes et al. |
| 5,424,054 A | 6/1995 | Bethune et al. |
| 5,454,880 A | 10/1995 | Sariciftci et al. |
| 5,648,128 A | 7/1997 | Yeh et al. |
| 5,690,807 A | 11/1997 | Clark, Jr. et al. |
| 5,744,399 A | 4/1998 | Rostoker et al. |
| 5,747,161 A | 5/1998 | Iijima |
| 5,908,585 A | 6/1999 | Shibuta |
| 5,914,151 A | 6/1999 | Usuki |
| 6,080,683 A | 6/2000 | Fauer et al. |
| 6,126,740 A | 10/2000 | Schulz et al. |
| 6,203,814 B1 | 3/2001 | Fisher et al. |
| 6,207,229 B1 | 3/2001 | Bawendi et al. |
| 6,277,766 B1 | 8/2001 | Ayers |
| 6,333,598 B1 | 12/2001 | Hsu et al. |
| 6,346,136 B1 | 2/2002 | Chen et al. |
| 6,348,295 B1 | 2/2002 | Griffith et al. |
| 6,559,375 B1 | 5/2003 | Meissner et al. |
| 6,645,455 B2 | 11/2003 | Margrave et al. |
| 6,683,783 B1 | 1/2004 | Smalley et al. |
| 6,685,986 B2 | 2/2004 | Oldenburg et al. |
| 6,710,366 B1 | 3/2004 | Lee et al. |
| 6,723,624 B2 | 4/2004 | Wang et al. |
| 6,755,530 B1 | 6/2004 | Loftus et al. |
| 6,770,497 B2 | 8/2004 | Ihm |
| 6,827,918 B2 | 12/2004 | Margrave et al. |
| 6,835,366 B1 | 12/2004 | Margrave et al. |
| 6,841,139 B2 | 1/2005 | Margrave et al. |
| 6,852,920 B2 | 2/2005 | Sager et al. |
| 6,863,942 B2 | 3/2005 | Ren et al. |
| 6,875,412 B2 | 4/2005 | Margrave et al. |
| 6,882,094 B2 | 4/2005 | Dimitrijevic et al. |
| 6,918,946 B2 | 7/2005 | Korgel et al. |
| 6,946,597 B2 | 9/2005 | Sager et al. |
| 6,969,897 B2 | 11/2005 | Kim, II |
| 6,970,239 B2 | 11/2005 | Chan et al. |
| 6,992,322 B2 | 1/2006 | Narayan |
| 7,087,832 B2 | 8/2006 | Scher et al. |
| 7,129,554 B2 * | 10/2006 | Lieber et al. ............... 257/414 |
| 7,253,014 B2 | 8/2007 | Barron et al. |
| 7,253,431 B2 | 8/2007 | Afzali-Ardakani et al. |
| 7,294,248 B2 | 11/2007 | Gao |
| 7,371,479 B2 | 5/2008 | Nuber |
| 2002/0094699 A1 | 7/2002 | Houng et al. |
| 2002/0110513 A1 | 8/2002 | Margrave et al. |
| 2002/0117659 A1 | 8/2002 | Lieber et al. |
| 2002/0130333 A1 | 9/2002 | Watanabe et al. |
| 2003/0065206 A1 | 4/2003 | Bolskar et al. |
| 2003/0132461 A1 | 7/2003 | Roesner et al. |
| 2003/0134433 A1 * | 7/2003 | Gabriel et al. ............... 436/518 |
| 2003/0179559 A1 | 9/2003 | Engelhardt et al. |
| 2003/0234978 A1 | 12/2003 | Garito et al. |
| 2004/0023317 A1 | 2/2004 | Motamedi et al. |
| 2004/0043527 A1 * | 3/2004 | Bradley et al. ............... 438/48 |
| 2004/0265209 A1 | 12/2004 | Colbert et al. |
| 2005/0089684 A1 | 4/2005 | Barron et al. |
| 2005/0119364 A1 | 6/2005 | Grah et al. |
| 2006/0036045 A1 | 2/2006 | Wilson et al. |
| 2006/0067870 A1 | 3/2006 | Park et al. |
| 2006/0186502 A1 | 8/2006 | Shimotani et al. |
| 2006/0249203 A1 | 11/2006 | Li et al. |
| 2007/0005116 A1 | 1/2007 | Lo |
| 2008/0171204 A1 | 7/2008 | Barron et al. |
| 2008/0233040 A1 | 9/2008 | Barron et al. |

FOREIGN PATENT DOCUMENTS

| | | | |
|---|---|---|---|
| EP | 1246205 A1 | 10/2002 | |
| GB | 2370408 A | 6/2002 | |
| JP | 08325195 | 12/1996 | |
| KR | 100649743 B1 | 11/2006 | |
| WO | 9921934 A1 | 5/1999 | |
| WO | WO 00/51186 * | 8/2000 | ............... 257/24 |
| WO | 0161753 A1 | 8/2001 | |
| WO | 02051782 A1 | 7/2002 | |
| WO | 02088024 A1 | 11/2002 | |
| WO | 03043934 A1 | 5/2003 | |
| WO | 2004042432 A2 | 5/2004 | |
| WO | 2004042432 A3 | 5/2004 | |
| WO | 2004044948 A2 | 5/2004 | |
| WO | 2004044948 A3 | 5/2004 | |
| WO | 2004046023 A2 | 6/2004 | |
| WO | 2004046023 A3 | 6/2004 | |
| WO | 2005000735 A2 | 1/2005 | |
| WO | 2005000735 A3 | 1/2005 | |
| WO | 2007041293 A2 | 4/2007 | |
| WO | 2007041293 A3 | 4/2007 | |
| WO | 2007084540 A2 | 7/2007 | |
| WO | 2007084540 A3 | 7/2007 | |

OTHER PUBLICATIONS

Kong et al., *Nanotube Molecular Wires as Chemical Sensors*, Science vol. 287, Jan. 28, 2000.

Foreign communication from a related counterpart application—Supplementary European Search Report of Application No. EP 03 78 6924, Mar. 26, 2009, 3 pages.

Foreign communication from a related counterpart application—Supplementary European Search Report of Application No. EP 03 81 6414, Mar. 27, 2009, 3 pages.

Kreupl, Franz, et al., "A status report on technology for carbon nanotube devices," Solid State Technology, Apr. 1, 2002, pp. S09/S10, S12, S14, S16, vol. 45, Issue 4, Penwell Corporation, Tulsa, OK.

O'Connell, Michael J., "Carbon Nanotubes Properties and Applications," 2006, pp. 90-104, CRC Press.

Office Action dated Aug. 5, 2009 (13 pages), U.S. Appl. No. 10/496,066, filed Nov. 17, 2004.

Balavoine, Fabrice, et al., "Helical crystallization of proteins on carbon nanotubes: a first step towards the development of new biosensors," Angew. Chem. Int. Ed, 1999, pp. 1912-1915, vol. 38, No. 13/14, Wiley-VCH Verlag GmbH.

Bronikowski, Michael J., et al., "Gas-phase production of carbon single-walled nanotubes from carbon monoxide via the HiPco process: a parametric study," Journal of Vacuum Science Technology, Jul./Aug. 2001, pp. 1800-1805, vol. 19, No. 4, American Vacuum Society.

Chen, Robert J., et al., "Noncovalent sidewall functionalization of single-walled carbon nanotubes for protein immobilization," Journal of the American Chemical Society, 2001, pp. 3838-3839, vol. 123, No. 16, American Chemical Society.

Collins, Philip G., et al., "Extreme oxygen sensitivity of electronic properties of carbon nanotubes," Science, Mar. 10, 2000, pp. 1801-1804, vol. 287, www.sciencemag.org.

Da Ros, Tatiana, et al., "Fullerene derivatives as potential DNA photoprobes," Australian Journal of Chemistry, 2001, pp. 223-224 plus cover, vol. 54, CSIRO Publishing, Australia.

Foreign communication from a related counterpart application, International Search Report, PCT/US02/37211, Mar. 10, 2003, 3 pgs.

Foreign communication from a related counterpart application, International Search Report, PCT/US03/37188, Dec. 21, 2004, 3 pgs.

Foreign communication from a related counterpart application, International Preliminary Examination Report, PCT/US03/37188, Sep. 30, 2005, 4 pgs.

Fu, Qiang, et al., "Selective coating of single wall carbon nanotubes with thin SiO2 layer," Nano Letters, 2002, pp. 329-332, vol. 2, No. 4, American Chemical Society.

Girifalco, L. A., et al., "Carbon nanotubes, buckyballs, ropes, and a universal graphitic potential," Physical Review B, Nov. 15, 2000, pp. 104-110, vol. 62, No. 19, The American Physical Society.

Kong, Jing, et al., "Functionalized carbon nanotubes for molecular hydrogen sensors," Advanced Materials, Sep. 14, 2001, pp. 1384-1386, vol. 13, No. 18, Wiley-VCH, Verlag GmbH.

Kuzumaki, Toru, et al., "Mechanical characteristics and preparation of carbon nanotube fiber-reinforced Ti composite," Advanced Engineering Materials, 2000, pp. 416-418, vol. 2, No. 7.

O'Connell, Michael J., et al., "Band-gap fluorescence from individual single-walled carbon nanotubes," Science, Jul. 26, 2002, pp. 593-596, vol. 297, www.sciencemag.org.

O'Connell, Michael J., et al., "Reversible water-solubilization of single-walled carbon nanotubes by polymer wrapping," Chemical Physics Letters, 2001, pp. 265-271, Elsevier.

Seeger, T., et al., "Nanotube composites: novel $SiO_2$ coated carbon nanotubes," Chem. Commun., 2002, pp. 1-5, Royal Society of Chemistry, Great Britain.

Seeger, T. et al., "$SiO_x$-coating of carbon nanotubes at room temperature," Chemical Physics Letters, 2001, pp. 41-46, vol. 339, Elsevier.

Thess, Andreas, et al., "Crystalline ropes of metallic carbon nanotubes," Science, Jul. 26, 1996, pp. 483-487, vol. 273, Issue 5274, American Association for the Advancement of Science. U.S.

Tsang, Shik Chi, et al., "Immobilization of platinated and iodinated oligonucleotides on carbon nanotubes," Angew. Chem. Int., Ed. Engl., 1997, pp. 2198-2200, vol. 36, No. 20, Wiley-VCH, Verlag GmbH.

Foreign communication from a related counterpart application, International Preliminary Examination Report, PCT/US02/37211, Dec. 4, 2003, 31 pgs.

Foreign communication from a related counterpart application, Written Opinion, PCT/US02/37211, Sep. 30, 2003, 5 pgs.

Banjerjee, Sarbajit, et al., "Synthesis and characterization of carbon nanotube-nanocrystal heterostructures," Nano Letters, 2002, pp. 195-200, vol. 2, No. 3, American Chemical Society.

Foreign communication from a related counterpart application—Supplementary European Search Report of Application No. EP 02 78 9769, Jan. 7, 2009, 8 pages.

Haremza, Joanne M., et al., "Attachment of single CdSe nanocrystals to individual single-walled carbon nanotubes," Nano Letters, 2002, pp. 1253-1258, vol. 2, No. 11, American Chemical Society.

Hernadi, K., et al., "Synthesis of MWNT-based composite materials with inorganic coating," Acta Materialia, 2003, pp. 1447-1452, vol. 51, Acta Materialia Inc., published by Elsevier Science Ltd.

Office Action (Final) dated Jan. 23, 2009 (19 pages), U.S. Appl. No. 10/496,066, filed Nov. 17, 2004.

Office Action dated Feb. 6, 2009 (25 pages), U.S. Appl. No. 11/834,471, filed Aug. 6, 2007.

Satishkumar, B. C., et al., "Oxide nanotubes prepared using carbon nanotubes as templates," Journal of Materials Research, Mar. 1997, pp. 604-606, vol. 12, No. 3, Materials Research Society.

Foreign communication from a related counterpart application—International Search Report and Written Opinion, PCT/US2008/063404, Sep. 12, 2008, 15 pages.

Foreign communication from a related counterpart application—International Search Report and Written Opinion, PCT/US2008/063076, Sep. 16, 2008, 13 pages.

Office Action dated Jun. 13, 2008 (7 pages), U.S. Appl. No. 10/496,066, filed Nov. 17, 2004.

Whitsitt, Elizabeth A., et al., "Silica coated single walled carbon nanotubes," Nano Letters, 2003, pp. 775-778, vol. 3, No. 6, American Chemical Society.

* cited by examiner

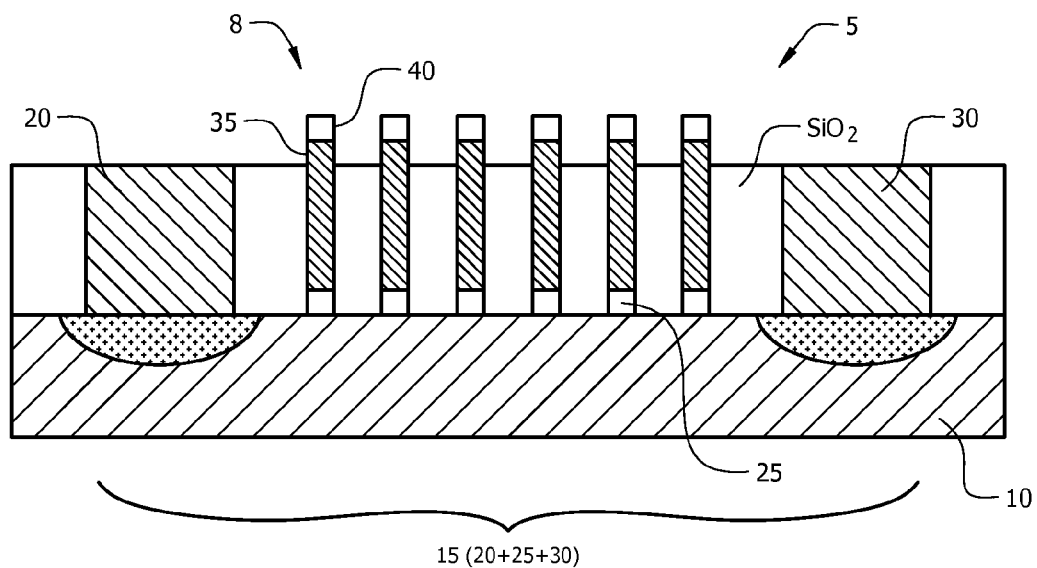

METHOD FOR CREATING A FUNCTIONAL INTERFACE BETWEEN A NANOPARTICLE, NANOTUBE OR NANOWIRE, AND A BIOLOGICAL MOLECULE OR SYSTEM

STATEMENT REGARDING FEDERALLY SPONSORED RESEARCH OR DEVELOPMENT

This work was sponsored by the Office of Naval Research under grant No. N00014-97-0213.

BACKGROUND OF THE INVENTION

1. Field of the Invention

This invention relates to the field of fullerenes and more specifically to the field of biochemical sensors comprising chemically sensitive field effect transistors having nanotubes.

2. Background of the Invention

An increasing interest has occurred in the development of chemical sensors in the identification of biological molecules or fragments. Such an increasing interest has been seen in a wide range of industries including clinical chemistry such as alternative site and critical care measurements, environmental detection of hazardous and mutagenic substances, in-line monitors for the food production industry, gene expression, and the like. For instance, determination of gene sequences is typically based upon spectroscopic characterization of dye molecules that are tagged to specific recognition molecules. The characteristic spectrum of the dye molecule detects binding of the dye molecule to a biological fragment such as DNA. Drawbacks of using the spectroscopy technique include limited sensitivity and selectivity of the technique.

Chemical sensors with enhanced sensitivity have been used for detection in such industries. A typical chemical sensor device is a chemically sensitive field effect transistor (chem-FET). Typical chem-FET devices have relied on the use of a porous dielectric layer into which a substance such as a chemical to be detected is absorbed. The dielectric constant of the dielectric layer is altered by such absorption, which results in a positive detection of the substance. Drawbacks to chem-FETs include a susceptibility to moisture. For instance, a dielectric layer sufficiently porous to allow for DNA will typically also allow water into the gate of the chem-FET, which can result in failure of the device. Consequently, chem-FET devices having carbon nanotubes have been used for such detection. The carbon nanotubes are usually used as a bridge between the source and the drain. The presence of certain molecules such as oxygen or ammonia can alter the overall conductivity of the carbon nanotube by the donation or acceptance of electrons. Selectivity in the carbon nanotubes is typically achieved by functionalizing a majority or all of the surface of the carbon nanotube through the placement of specific functional groups on the nanotube surface, with such functional groups having the ability to selectively bind specific target molecules. Drawbacks of such chem-FETs comprising carbon nanotubes include functionalization changing the electronic properties from that of a semiconductor to that of an insulator. Further drawbacks include the diversity of tube diameters, chiral angles, and aggregation states of the tubes.

Consequently, there is a need for a more efficient chem-FET having improved selectivity and sensitivity. Further needs include a chem-FET that is not susceptible to damage by absorption of water through the dielectric layer. Additional needs include a chem-FET with carbon nanotubes that maintain their semiconductivity.

BRIEF SUMMARY OF SOME OF THE PREFERRED EMBODIMENTS

These and other needs in the art are addressed in one embodiment by an inventive field effect transistor. The field effect transistor comprises a source; a drain; a gate; at least one carbon nanotube on the gate; and a dielectric layer that coats the gate and a portion of the at least one carbon nanotube, wherein the at least one carbon nanotube has an exposed portion that is not coated with the dielectric layer, and wherein the exposed portion is functionalized with at least one indicator molecule.

In other embodiments, the invention comprises a method for making a transistor. The method comprises providing a field effect transistor comprising a source, a gate, and a drain, wherein at least one nanotube is on the gate; coating the at least one nanotube and the gate with a dielectric layer; etching a portion of the at least one nanotube to provide an exposed nanotube portion; and functionalizing the exposed nanotube portion.

In a further embodiment, the invention comprises a biochem-FET. The biochem-FET comprises a FET having a gate; at least one carbon nanotube on the gate; and a dielectric layer that coats the gate and a portion of the at least one carbon nanotube, wherein the at least one carbon nanotube has an exposed portion that is not coated with the dielectric layer; and at least one indicator molecule on the exposed portion.

An additional embodiment of the invention comprises a biochem-FET array. The biochem-FET array comprises a plurality of biochem-FETs wherein each biochem-FET comprises a FET having a gate; at least one carbon nanotube on the gate; a dielectric layer that coats the gate and a portion of the at least one carbon nanotube; wherein the at least one carbon nanotube has an exposed portion that is not coated with the dielectric layer; and at least one indicator molecule on the exposed portion; and a substrate.

In alternative embodiments, the carbon nanotube is a single-walled carbon nanotube. Further alternative embodiments include the dielectric layer comprising silica.

It will therefore be seen that a technical advantage of the present invention includes an improved field effect transistor that overcomes the problem of external attack of the gate. The gate is protected from external attack by the dielectric layer obscuring the surface of the gate. Further advantages include overcoming the problem of a functionalized nanotube changing from a semiconductor to an insulator and that nanotubes are themselves sensitive to external chemical environments (J. Kong, N. R. Franklin, C. W. Zhou, M. G. Chapline, S. Peng, K. J. Cho, and H. J. Dai, "Nanotube molecular wires as chemical sensors," *Science*, 2000, 287, 622-625). Such a change typically adversely affects operation of the field effect transistor (P. G. Collins, K. Bradley, M. Ishigami, and A. Zettl, "Extreme oxygen sensitivity of electronic properties of carbon nanotubes," *Science*, 2000, 287, 1801-1804).

The foregoing has broadly outlined the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawing in which the drawing illustrates a biochem-FET array having a plurality of biochem-FETs.

DETAILED DESCRIPTION OF THE PREFERRED EMBODIMENTS

The Biochem-FET

The drawing illustrates a biochem-FET array 5 comprising a plurality of biochem-FETs 8 and a substrate 10. Substrate 10 can be any shape and comprise any components suitable for supporting field effect transistors (FETs). Without limiting the invention, examples of suitable components for base 10 include silicon, germanium, GaAs, or InP, preferably silicon. Biochem-FET 8 comprises a FET 15 and a nanotube 35. FET 15 comprises a source 20, a gate 25, and a drain 30. FETs are well known in the art, and FET 15 can comprise any FET suitable for use in biochem-FET 8 of the present invention. Without limiting the present invention, FET 15 is an example of a typical FET comprising a source 20, a gate 25, and a drain 30. Sources for FETs are well known in the art, and source 20 can comprise any suitable source that can be formed as known to one of ordinary skill in the art. Gates for FETs are well known in the art, and gate 25 can comprise any suitable gate for use in biochem-FET 8 of the present invention. Drains for FETs are well known in the art, and drain 30 can comprise any suitable drain that can be formed as known to one of ordinary skill in the art. Without limiting the scope of the invention, examples of suitable materials for source 20, gate 25, and drain 30 include metallic wires, gold, platinum, copper, chromium, titanium, and the like.

As illustrated on the drawing, biochem-FET 8 comprises one nanotube 35. In alternative embodiments (not illustrated), biochem-FET 8 can comprise more than one nanotube 35. Nanotube 35 comprises carbon nanotubes, which are well known in the art and are a type of fullerene having an elongated, tube-like shape of fused six-membered and five-membered rings. Carbon nanotubes can be single walled carbon nanotubes or multi-walled carbon nanotubes. Single-walled carbon nanotubes differ from multi-walled carbon nanotubes by the number of tubes. Single-walled carbon nanotubes comprise one tube about a given center, and multi-walled carbon nanotubes comprise at least two nested tubes about a common center. When biochem-FET 8 comprises one nanotube 35, nanotube 35 can be a single-walled nanotube or a multi-walled nanotube. When chem-FET 5 comprises more than one nanotube 35, the nanotubes 35 can be single-walled nanotubes, multi-walled nanotubes, or mixtures thereof. Nanotubes 35 are coated with a dielectric and preferably at least a portion of the surface of the coated nanotube 35 is etched.

A Method of Making the Biochem-FET

The present invention provides a method for making biochem-FET 8, with the method comprising the steps of (A) providing a FET 15 comprising a source 20, a gate 25, and a drain 30, wherein at least one nanotube 35 is on the gate 25; (B) coating the at least one nanotube 35 and the FET 15 with a dielectric; (C) etching at least a portion of the dielectric coating on the at least one nanotube 35 to provide an exposed nanotube portion 40; and (D) functionalizing the exposed nanotube portion 40.

The at least one nanotube 35 is preferably grown or attached on gate 25. Processes for growing and attaching nanotubes are well known in the art, and the present invention includes any suitable process for growing or attaching nanotubes 35 on gate 25. In growing nanotubes 35, preferably, an aperture or hole is located at a desired position on gate 25. The aperture or hole can be formed by any available methods such as laser drilling, wet etching, and dry etching. After locating the hole at the desired location, a catalyst is placed in the aperture or hole. Catalysts for growing nanotubes are well known in the art, and the present invention can include any catalyst suitable for growing nanotubes 35. Examples of suitable catalysts include metal, metal alloy, superconducting metal, metal cluster compounds and any other suitable catalyst. The catalysts are then synthesized by synthesizing methods to grow nanotubes 35. Preferably, nanotubes 35 are grown in a vertical direction. Synthesizing methods are well known in the art, and the present invention can include any suitable synthesizing method. Without limiting the invention, examples of suitable synthesizing methods include catalyst thermal decomposition, laser vaporization and arc discharge, plasma enhanced chemical vapor deposition, and hot-filament vapor deposition.

Attaching nanotube 35 comprises attaching a preformed nanotube to gate 25 by reaction of a chemically functionalized surface of gate 25 with an appropriately functionalized nanotube. Methods for functionalizing silica or metal surfaces are well known in the art, and methods for providing functionalization of nanotubes are also well known in the art. A typical functionalization of a nanotube is through the formation of carboxylate groups on the ends of the nanotubes.

FET 15 and nanotube 35 are coated with a dielectric layer. In alternative embodiments, nanotube 35 and gate 25 are coated with a dielectric layer. Coating nanotubes is well known in the art, and FET 15 and nanotube 35 can be coated by any suitable process. For instance, liquid phase deposition, chemical vapor deposition, electrochemical deposition, and sol-gel can be used as coating processes, preferably liquid phase deposition. Preferably, the coating is sufficient to prevent substances such as chemicals, water, oxygen, organic acids, citric acid, and other chemicals present in the detection mixture that are not to be detected from contacting FET 15 and nanotube 35. The coating can be any thickness suitable for preventing such contact. Preferably, the coating thickness is 1-100 nm. More preferably, the coating thickness is 1-20 nm. Suitable coatings include silica or other oxides that have dielectric properties and are chemically inert under the required application conditions of the chem-FET. Preferably, the coating comprises silica. Without limiting the invention, a dielectric layer comprising silica is coated on gate 25 and nanotube 35 by contacting gate 25 and nanotube 35 with a solution comprising silica. The silica is preferably at least partially dissolved in the solution. More preferably, the solution comprises $H_2SiF_6$. Without being bound by any particular theory, it is believed that fluorosilicic acid can react with a base to produce silica, as shown in Equation (1).

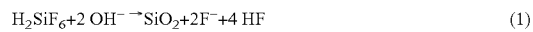  (1)

Chemically functionalized substrates, such as hydroxylated $C_{60}$, can react with the acid in a condensation reaction, in turn acting as a nucleation site to begin layer growth as shown in Equation (2).

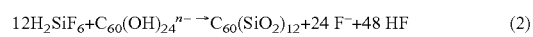  (2)

Growth occurs at the initial silicate and reacts with additional fluorosilicic acid to grow layers of silica on the particle. In an alternative embodiment, the nanotubes may be functionalized by the addition of a surfactant. The growth of the dielectric thus occurs within the surfactant coating.

In alternative embodiments, biochem-FET 8 comprises more than one dielectric layer. In such alternative embodiments, the dielectric layers can be the same or different coatings.

The top end of coated nanotube 35 is etched to remove the coating and provide an exposed nanotube portion 40. Exposed nanotube portion 40 preferably comprises the tip of nanotube 35. In alternative embodiments, exposed nanotube portion 40 comprises a portion of nanotube 35 greater than the tip. Etching coated nanotubes is well known in the art, and the coated nanotubes 35 of the present invention can be etched by any suitable etching process. Examples of suitable etching processes include plasma reactive etching, chemical acid etching, reactive ion etching, hydrofluoric acid (HF), hydrochloric acid, and the like. Preferably, the etching process is by hydrofluoric acid. It is required that sufficient surface of the nanotube be exposed during the etch step to allow for functionalization or interaction with an indicator molecule.

Functionalizing exposed nanotube portion 40 comprises attaching at least one indicator molecule to exposed nanotube portion 40. Functionalizing nanotubes is well known in the art. Preferable techniques for functionalizing exposed nanotube portion 40 include chemical functionalization. Chemical functionalization includes any chemical reaction that modifies and/or adds chemical groups to the surface of exposed nanotube portion 40, which can be used to deposit reactive groups on the surface of exposed nanotube portion 40. Any chemical reaction known in the art can be used to functionalize exposed nanotube portion 40. Without limiting the invention, examples of suitable chemical reactions include hydroxylation, oxidation to form carboxylate groups, epoxidation, and reaction with a suitable organic reagent to create a functional group such as an organic hydroxide. The preferable chemical reaction is hydroxylation, which is well known in the art. It is believed that the dielectric coating protects FET 15 and non-exposed portion of carbon nanotube 35. Indicator molecules of the present invention include any molecule that is attachable to exposed nanotube portion 40. Preferable indicator molecules include molecules that are chemically sensitive and interact with a target molecule. The target molecule is preferably a biological group, but it is to be understood that the target molecule can comprise any chemical. Most preferably, the indicator molecule is a DNA oligo or a polypeptide. The DNA oligo can be any suitable DNA oligo, preferably a DNA oligo specific for a target molecule comprising a DNA sequence. It has not been demonstrated, but it is believed that binding of a target molecule to the indicator molecule will cause an electric charge to pass from the target molecule to carbon nanotube 35. Carbon nanotube 35 conducts the electric charge to FET 15. Biochem-FET 8 preferably transmits such an electric charge to a computer or other device suitable for recording and analyzing the charge. Analyzation of the charge can be accomplished for a wide variety of applications. Without limiting the invention, examples of such applications include DNA genotyping, sensing of particular DNA sequences, and sensing of particular proteins.

It is to be understood that biochem-FET array 5 can comprise biochem-FETs 8 that have the same indicator molecules or can comprise biochem-FETs 8 having different indicator molecules from each other. It is to be further understood that each biochem-FET 8 can have one or more than one type of indicator molecule.

To further illustrate various illustrative embodiments of the present invention, the following examples are provided.

EXAMPLES

Examples 1-3

Examples 1-3 are examples of functionalization of a fullerene.

Example 1

1,2-(4'-oxocyclohexano)fullerene 2-trimethylsilyloxy-1,3-butadiene (0.248 g) in 20 mL dried degassed toluene was added drop-wise to a refluxing solution of 1.00 g fullerene in 350 mL toluene under nitrogen. The solution refluxed for 24 h and then cooled to room temperature. Toluene was evaporated off under vacuum and mild heat (ca.40° C.). The resulting crude product was dissolved in a minimal amount of carbon disulfide and loaded on a column packed with silica flash gel in hexanes. Unreacted fullerene (purple) was eluted with a carbon disulfide/hexanes 1:1 and then product (dark brown) was eluted with toluene. Toluene was roto-vapped off before mild heating under vacuum to give dry crystalline product.

Example 2

1,2-(4'-hydroxycyclohexano)fullerene

A slight excess of DIBAL-H (~1 mL) was added via syringe to a solution of 0.300 g 1,24'-oxocyclohexano) fullerene in dry toluene and stirred overnight at room temperature. 40 mL of saturated ammonium chloride solution was added, and the solution was stirred for 3 h. The organic layer separated and the aqueous layer was extracted with toluene (2×50 mL). The combined organic phases were dried over sodium sulfate and followed by evaporation of the solvent. Flash chromatography on a column of silica with toluene followed by evaporation produced a reddish dark brown solid.

Example 3

1,2-(4'-bromoacetyloxycyclohexano)fullerene 0.62 mL bromoacetyl bromide was added to a solution of 0.120 g 1,2-(4'-hydroxycyclohexano)fullerene and 80 mL dry toluene. The solution was refluxed 1 h and then the solvent was evaporated. Elution through a column of silica with toluene afforded, after evaporating the solvent and drying under vacuum and heat, a dark brown solid.

Example 4

Example 4 demonstrates attachment of an indicator molecule to a fullerene.

Example 4 oligonucleotide attachment to 1,2-(4'-bromoacetyloxycyclohexano)fullerene

Using a 3:1 molar ratio of oligonucleotide to derivitized fullerene, 39 nmole oligo in 50 μL water was added to 195 μL of a 0.6 mM solution 1,2-(4'-bromoacetyloxycyclohexano)

fullerene in DMF. This solution was diluted to 500 μL and then 500 μL distilled chloroform was added.

Examples 5-6

Examples 5-6 demonstrate coating nanotubes with a suitable dielectric.

Example 5

Fumed silica (3.0 g) was added to 50 mL of 3.20 M fluorosilicic acid solution ($H_2SiF_6$: Riedel de Haen, 34% pure) and allowed to stir overnight. This solution was then filtered by vacuum through a 0.22 micron Millipore filter. The filtrate was diluted to 1.0 M with UP water. A portion of this solution (100 mL) was added to a 1% SDS solution (1 mL) containing dispersed single walled carbon nanotubes (SWNT, 50 mg/L). These were allowed to react in a plastic centrifuge tube, with stirring, at 30° C. for four hours. The reaction was then quenched with ethanol and centrifuged at 4400 rpm for 15 minutes.

Example 6

Fumed silica (3.0 g) was added to 50 mL of 3.20 M fluorosilicic acid solution ($H_2SiF_6$: Riedel de Haen, 34% pure) and allowed to stir overnight. This solution was then filtered, by vacuum, through a 0.22 micron Millipore filter. The filtrate was diluted to 1.0 M with UP water. A portion of this solution (5 mL) was added to a 1% SDS solution (5 mL) containing dispersed SWNT (50 mg/L). These were allowed to react in a plastic centrifuge tube, with stirring, at 30° C. for four hours. The reaction was then quenched with ethanol to yield silica coated SWNT.

Example 7

Example 7 demonstrates etching of silica SWNTs.

Example 7

Products from Examples 5 and 6 were dried on a surface and selectively etched with hydrofluoric acid (1%). They were then thoroughly rinsed with UP water and dried for characterization.

Although the present invention and its advantages have been described in detail, it should be understood that various changes, substitutions and alterations may be made herein without departing from the spirit and scope of the invention as defined by the appended claims.

What is claimed is:

1. A field effect transistor comprising:
a source;
a drain;
a gate;
a dielectric layer that coats the gate; and
at least one carbon nanotube disposed at least partially in said dielectric layer, said at least one carbon nanotube having a portion which is functionalized with at least one indicator molecule that is exposed from the dielectric layer, the at least one carbon nanotube being on the gate for transmitting charge from the at least one indicator molecule to the gate.

2. The field effect transistor of claim 1, wherein the at least one carbon nanotube is a single-walled carbon nanotube.

3. The field effect transistor of claim 1, wherein the dielectric layer comprises silica.

4. The field effect transistor of claim 1, wherein the dielectric layer coats the source and the drain.

5. The field effect transistor of claim 1, wherein the indicator molecule is a DNA oligo.

6. The field effect transistor of claim 5, wherein the DNA oligo is specific for a DNA sequence.

7. The field effect transistor of claim 1, wherein the indicator molecule is a polypeptide.

8. The field effect transistor of claim 1, wherein the field effect transistor is a biochem-FET.

9. A method for making a transistor, comprising:
(A) providing a field effect transistor comprising a source, a gate, and a drain, wherein at least one nanotube is on the gate;
(B) coating the at least one nanotube and the gate with a dielectric layer;
(C) etching a portion of the dielectric layer to provide an exposed nanotube portion; and
(D) functionalizing the exposed nanotube portion so that the at least one carbon nanotube is effective to transmit charge from the functionalized nanotube portion to the gate.

10. The method of claim 9, wherein the transistor is a biochem-FET.

11. The method of claim 9, wherein step (A) further comprises growing the at least one nanotube to provide the at least one nanotube on the gate.

12. The method of claim 9, wherein step (A) further comprises attaching the at least one nanotube to the gate to provide the at least one nanotube on the gate.

13. The method of claim 9, wherein step (B) is accomplished by liquid phase deposition.

14. The method of claim 9, wherein step (B) further comprises coating the source and the drain.

15. The method of claim 9, wherein the dielectric layer comprises silica.

16. The method of claim 9, wherein step (C) is accomplished by HF.

17. The method of claim 9, wherein step (D) is accomplished by chemical functionalization.

18. The method of claim 17, wherein chemical functionalization comprises hydroxylation.

19. The method of claim 9, wherein functionalizing the exposed nanotube portion of step (D) comprises attaching at least one indicator molecule to the exposed nanotube portion.

20. The method of claim 19, wherein the at least one indicator molecule is chemically sensitive and interacts with at least one target molecule.

21. The method of claim 19, wherein the indicator molecule comprises a DNA oligo.

22. The method of claim 21, wherein the DNA oligo is specific for a target molecule comprising a DNA sequence.

23. The method of claim 19, wherein the indicator molecule comprises a polypeptide.

24. A biochem-FET, comprising:
a FET having a gate;
a dielectric layer that coats the gate; and
at least one carbon nanotube disposed at least partially in said dielectric layer, said at least one carbon nanotube having a portion which is functionalized with at least one indicator molecule that is exposed from the dielectric layer,
the at least one carbon nanotube being on the gate for transmitting charge from the at least one indicator molecule to the gate.

25. The biochem-FET of claim 24, wherein the at least one carbon nanotube is a single-walled carbon nanotube.

26. The biochem-FET of claim 24, wherein the dielectric layer comprises silica.

27. The biochem-FET of claim 24, wherein the at least one indicator molecule comprises a DNA oligo.

28. The biochem-FET of claim 27, wherein the DNA oligo is specific for a target molecule comprising a DNA sequence.

29. The biochem-FET of claim 24, wherein the at least one indicator molecule comprises a polypeptide.

30. A biochem-FET array, comprising:
a plurality of biochem-FETs wherein each biochem-FET comprises
a FET having a gate;
a dielectric layer that coats the gate;
at least one carbon nanotube;
disposed at least partially in said dielectric layer, said at least one carbon nanotube having a portion which is functionalized with at least one indicator molecule that is exposed from the dielectric layer, the at least one carbon nanotube being on the gate for transmitting charge from the at least one indicator molecule to the gate.

31. The biochem-FET array of claim 30, wherein the at least one carbon nanotube is a single-walled carbon nanotube.

32. The biochem-FET array of claim 30, wherein the dielectric layer comprises silica.

33. The biochem-FET array of claim 30, wherein the at least one indicator molecule comprises a DNA oligo.

34. The biochem-FET array of claim 33, wherein the DNA oligo is specific for a target molecule comprising a DNA sequence.

35. The biochem-FET array of claim 30, wherein the at least one indicator molecule comprises a polypeptide.

36. The biochem-FET array of claim 30, wherein the substrate comprises silicon.

* * * * *

UNITED STATES PATENT AND TRADEMARK OFFICE
CERTIFICATE OF CORRECTION

| | | |
|---|---|---|
| PATENT NO. | : 7,692,218 B2 | Page 1 of 1 |
| APPLICATION NO. | : 10/534431 | |
| DATED | : April 6, 2010 | |
| INVENTOR(S) | : Andrew R. Barron et al. | |

It is certified that error appears in the above-identified patent and that said Letters Patent is hereby corrected as shown below:

In column 1, lines 9-10, replace

"This work was sponsored by the Office of Naval Research under grant No. N00014-97-0213."

with

--This invention was made with government support under Grant Number N00014-97-0213 awarded by the Office of Naval Research. The government has certain rights in the invention.--

Signed and Sealed this
Twenty-seventh Day of September, 2011

David J. Kappos
*Director of the United States Patent and Trademark Office*